(12) United States Patent
Lee et al.

(10) Patent No.: US 7,012,156 B2
(45) Date of Patent: Mar. 14, 2006

(54) PREPARATION METHOD OF METHACRYLIC ACID

(75) Inventors: Ki-Hwa Lee, Taejon (KR); Jin-Sun Yoo, Flossmoor, IL (US)

(73) Assignee: Samsung General Chemicals, Co., Ltd., Chungnam (KR)

( * ) Notice: Subject to any disclaimer, the term of this patent is extended or adjusted under 35 U.S.C. 154(b) by 0 days.

(21) Appl. No.: 10/130,833

(22) PCT Filed: Dec. 20, 2000

(86) PCT No.: PCT/KR00/01497

§ 371 (c)(1),
(2), (4) Date: Sep. 27, 2002

(87) PCT Pub. No.: WO01/47857

PCT Pub. Date: Jul. 5, 2001

(65) Prior Publication Data

US 2003/0149300 A1     Aug. 7, 2003

(30) Foreign Application Priority Data

Dec. 24, 1999 (KR) ............... 1999-61854

(51) Int. Cl.
*C07C 51/16*     (2006.01)
(52) U.S. Cl. .................. 562/532; 566/535
(58) Field of Classification Search ............ 562/512, 562/598, 523, 531, 534, 535
See application file for complete search history.

(56) References Cited

U.S. PATENT DOCUMENTS

| | | | |
|---|---|---|---|
| 4,621,155 A | 11/1986 | Ueshima et al. | |
| 4,925,980 A | * 5/1990 | Matsumoto et al. | 562/534 |
| 4,985,592 A | 1/1991 | Ishii et al. | |

FOREIGN PATENT DOCUMENTS

GB     2104512     *  3/1983

OTHER PUBLICATIONS

European Patent Publication No. 0 454 376, Shinji et al., Oct. 10, 1991 (English).
European Patent Publication No. 0 580 901, Tazaki et al., Feb. 2, 1994 (English).
Japanese Patent Publication No. 57-171443, Rikuo et al., Oct. 22, 1982 (Abstract only, English).
Japanese Patent Publication No. 55-79340, Yoshio et al., Jun. 14, 1980 (Abstract only, English).
Japanese Patent Publication No. 61-005043, Masahiro et al., Jan. 10, 1986 (Abstract only, English).

* cited by examiner

*Primary Examiner*—Johann Richter
*Assistant Examiner*—Karl Puttlitz
(74) *Attorney, Agent, or Firm*—Meyertons, Hood, Kivlin, Kowert & Goetzel, P.C.; Eric B. Meyertons

(57) ABSTRACT

The present invention relates to a preparation method of methacrylic acid which improves reaction selectivity of methacrylic acid. The method may include producing methacrylic acid by gas phase oxidation of methachrolane in the presence of catalyst. Particularly, the present invention relates to the preparation method of methacrylic acid comprising the step of introducing $CO_2$ up to 3~80 mole % of the feed gas in the presence off catalyst having the general formula of $P_a Mo_{11} V_b X_c Y_d O_e$. X may be one or more elements selected from the group of alkaline metal and Tl element. Y may be one or more elements selected from the group of Cu, Pb, Sb, Cr and Ce. In addition, a, b, c, d and e are the molar ratio of each necessary element when molybdenum is 11; where a is 0.8~1.6, b is 0.6~2, c is 0.8~2.2, d is 0.1~0.8 and e is a suitable value for elemental valency in the composition of said formula respectively.

7 Claims, No Drawings

PREPARATION METHOD OF METHACRYLIC ACID

This application is a 371 of PCT/KR00/01497 Dec. 20, 2000.

TECHNICAL FIELD

The present invention relates to a method for producing methacrylic acid, which improves reaction selectivity of methacrylic acid while producing methacrylic acid by gas phase oxidation of methacrolein in the presence of catalysts.

BACKGROUND ART

Studies about a method for preparing methacrylic acid with high selectivity have been carried out concerning catalysts used in the methacrylic acid preparation by gas phase oxidation of methacrolein and among patent literatures. The main categories of the inventions are about the heteropoly acid catalysts since it is known to show good activity.

The heteropoly acid, however, has many disadvantageous basic properties for solid catalysts having insufficient catalytic capacity. Consequently it was difficult to apply commercially. The main disadvantages of the heteropoly acid catalysts are difficulties in getting consistent results, weak mechanical strength, and short life cycle of the catalysts. Other disadvantages to overcome are that the conversion rate and selectivity sharply decrease when unsaturated hydrocarbon and aromatic compounds are contaminated in the reactants. Mostly, the methacrolein is obtained by a catalyzed oxidation of isobutylene, wherein unreacted isobutylene and byproducts such as toluene and xylene etc., affect the capacity of the catalysts for the preparation of methacrylic acid thereby reducing the conversion rate and selectivity.

Many attempts to overcome said disadvantages have been disclosed in patent specifications. For example, there was an attempt to increase the selectivity of the catalysts by adding arsenic in the catalyst composition, but the problem was that the life cycle of the catalyst was short because of sublimation properties in the arsenic. There was another attempt to ensure the consistency of the catalysts and to increase the selectivity for methacrylic acid (European Patent Publication 0454376, Japanese Patent Publication So 57-171443, U.S. Pat. No. 4,621,155) and these purposes have been satisfied. The problem, however, was that the catalysts have low mechanical strength and the selectivity for methacrylic acid is low when the methacrolein obtained from oxidation of isobutylene, not the pure methacrolein, is used.

Furthermore, to increase the mechanical strength of the catalysts, for example, the mechanical strength can be increased by using sulfuric acid salts of metal. The problem was the capacity of the catalysts is too low (Japanese Patent Publication So 55-79340). The strength can also be increased by adding ceramic whiskers such as silicon carbide or silicon nitride etc., but there are many difficulties in applying it in reality because the ceramic whiskers are too expensive.

It is very important to maintain the selectivity for methacrylic acid particularly because the preparation method for methacrylic acid is commonly composed of a recycling process of the unreacted methacrolein due to instability of methacrolein and low heat stability of heteropoly acid catalysts.

DETAILED DESCRIPTION OF EMBODIMENTS

The purposes of this invention are to overcome the above-mentioned problems and are to provide a new preparation method for methacrylic acid with high selectivity for methacrylic acid.

The preparation method for methacrylic acid of the present invention is a method for preparing methacrylic acid by gas phase oxidation of methacrolein comprising the step of introducing $CO_2$ up to 3~80 mol % of the feed gas in the presence of a catalyst having general formula (I), $$P_a Mo_{11} V_b X_c Y_d O_e \qquad (I)$$

wherein, X is one or more elements selected from the group of alkaline metal and thallium (Tl) element, Y is one or more elements selected from the group of Cu, Pb, Sb, Cr and Ce, and a, b, c, d and e is the molar ratio of each necessary element when molybdenum is 11, where a is 0.8~1.6, b is 0.6~2, c is 0.8~2.2, d is 0.1~0.8 and a is a suitable value for valency in the formula (I).

The preparation method for the said catalyst of the general formula (I) in the preparation method for the methacrylic acid is as follows:

Weigh phosphomolybdenic acid and vanadium oxide or phosphoric acid, molybdenic oxide and vanadium oxide as much as the composition rate of the desired catalyst and mix with water. The concentration in the basis of molybdenum may be 0.01~7, or 0.02~4 molar concentration. After obtaining reddish solution by refluxing the above mixtures via heating for 1~20 hours, maintain the temperature in the range of 0~100° C. An aqueous solution of quaternary ammonium salts or alkylpyridinium salts or pyridine etc. may be added and may function as the precipitating agent of heteropoly acid (referring as compound Q), so that the molar ratio in the basis of molybdenum 11 is 1~8. In another embodiment, the X, Y element, which is a cocatalyst element with the said compound Q, may be added in the desired catalyst composition rate. At this time the starting compound for cocatalyst element can be used, and may include any type of compound such as nitric acid salts, hydrochloride acid salts, acetic acid salts or oxides etc. When only the compound Q is added to the mixtures, the cocatalyst elements can be added after the precipitates obtained by filtering the produced suspension are redispersed into water. In other embodiments, it may be also possible to directly mix the cocatalyst elements with the produced suspension without a filtering process. When the filtering process is omitted or the cocatalyst compound with the compound Q is added, the produced precipitates can be dried by filtration. In other embodiments, after evaporating the water by heating at the temperature range of 50~100° C. without the filtering process, the obtained slurry is dried at the temperature range of 90~180° C., preferably 90~150° C. The dried catalyst lump may be smashed. Particles less than 60 mesh size may be selected and then molded. Any kind of molding method i.e., tableting molding, extrusion molding, spheroid formation and coating molding etc. can be used. The molded catalysts can have various size and shapes, for example, tablet, rod shape, spheroidal shape, hollow-type etc. The molded catalysts may be plasticized for 1~10 hours, at temperature increasing at the rate of 0.1~10° C./min, preferably at the rate of 0.2~5° C./min up to 300~420° C. in the atmosphere of oxygen/nitrogen—volume ratio of 0.1~20, preferably 0.1~15. There can be a holding time where temperature is halted without directly increasing temperature up to final temperature.

In the preparation method for the methacrylic acid, $CO_2$ is introduced into the feed gas which is fed into the reactor at least at 3~80 molar percent, or in other embodiments at 4~20 molar percent, or in some embodiment 5~15 mol % to prepare the methacrylic acid with high selectivity in the preparation reaction for methacrylic acid by gas phase oxidation of methacrolein. If the amount of the $CO_2$ introduction is less than 3 molar percent, the effect may be very low. If the amount of the $CO_2$ introduction is more than 80 molar percent, the selectivity for methacrolein may not increase.

In the preparation method for the methacrylic acid of the present invention, the reactor to prepare methacrolein by gas phase oxidation of methacrolein may be a tubular reactor comprising a jacket to control the temperature by circulating the heat medium. Said cylindrical reactor may also comprise a flow meter, flow controlling valve and measuring pump etc. The flow of compounds introduced into the reactor such as methacrolein, oxygen, $CO_2$, water and nitrogen etc. may be finely controlled and then introduced into the reactor.

In an embodiment of the preparation method for methacrylic acid, methacrylic acid can be prepared by first charging the reactor with the said prepared catalyst and by oxidizing methacrolein using the following reaction conditions: a reaction temperature of about 260~330° C.; a space velocity of about 700~2,000 $hr^{-1}$; a methacrolein concentration of about 2~5 mol %; and about 0.5~5 kg of reaction pressure on the basis of absolute pressure, about 2.0~3.5 of the molar ratio between oxygen and methacrolein, and CO2 introduction of at least about 3~80 mol % of a feed gas.

The present invention is described in further detail in the following examples and comparative examples, which are not intended to limit the scope of the present invention but to describe only for the illustrative purposes.

EXAMPLES

The following examples are included to demonstrate certain embodiments. It should be appreciated by those of skill in the art that the techniques disclosed in the examples which follow represent techniques discovered which function well in the practice of the disclosure herein. However, those of skill in the art should, in light of the present disclosure, appreciate that many changes can be made in the specific embodiments which are disclosed and still obtain a like or similar result without departing from the spirit and scope of the invention.

Preparing the Catalysts

A reddish aqueous solution (solution A) was obtained by mixing 3 kg of molybdenum trioxide. 172 g of vanadium pentoxide and 85% of phosphoric acid with 15L of water while vigorously stirring and then by refluxing the mixture for about 5 hours. 598 g of pyridine, 286 g of potassium nitrate, 137 g of cupric nitrate trihydrate were dissolved into 5L of water (solution B). After a yellowish suspension was obtained by mixing solution A and B while vigorously stirring, the suspension was ripened by heating at about 70° C. for 5 hours and then the water was evaporated. The obtained slurry was dried in a electric furnace at about 120° C. The dough that was made by smashing the dried lump under 60 mesh size, putting into the kneader and by adding 1% of starch aqueous solution into the kneader was molded into the molded catalysts having the size of diameter 6 mm×length 5 mm in the extruder. The molded catalysts was plasticized by increasing the temperature up to 220° C. at the rate of 0.5° C./min and held for 1 hour, and again increasing the temperature up to 360° C. at the rate of 0.5° C./min and held for 5 hours. The composition of the prepared catalysts was $P_{1.2}Mo_{11}V_1Cu_{0.3}K_{1.5}$.

Comparative Example 1

The reaction to prepare methacrylic acid was conducted by charging the prepared catalysts into a cylindrical reactor comprising a jacket, which was used to control temperature by circulating heat medium, and of which inner diameter was 25 mm and length was 3 m. The above mentioned reaction was conducted continuously in the conditions of 290° C. temperature of heat materials in the jacket, 1,000 $hr^{-1}$ of space velocity (GHSV, $hr^{-1}$), which is a value of flow over catalysts volume at the standard condition (0° C., 1 atmosphere) of the whole reaction mixture gas introduced into the reactor, 3.0% of the concentration of methacrolein the reactant, 3.0 of the molar ratio between oxygen and mathacrolein, 11% of the content of water vapor, 77% of nitrogen which was to adjust the balance of the other content and the atmosphere of the reaction pressure. The reaction result is summarized in Table 1.

Example 1

The reaction to prepare methacrylic acid by oxidation of methacrolein was conducted by the same way as in Comparative Example 1 except that the content of nitrogen was reduced to 5 mol % and 5 mol % of $CO_2$ was introduced in the composition of the inlet gas which was fed into the reactor. The result of the reaction is shown in Table 1.

Example 2

The reaction to prepare methacrylic acid by oxidation of methacrolein was conducted by the same way as in Comparative Example 1 except that the content of nitrogen was reduced to 9 mol % and 9 mol % of $CO_2$ is introduced in the composition of the inlet gas which was fed into the reactor. The result of the reaction is shown in Table 1.

Example 3

The reaction to prepare methacrylic acid by oxidation of methacrolein was conducted in the same conditions as in Example 1 by increasing the $CO_2$ concentration 5 mol % and reducing the nitrogen content again after the reaction was conducted in the conditions of the example 2. The result of the reaction is shown in Table 1.

Comparative Example 2

The reaction to prepare methacrylic acid by oxidation of methacrolein was conducted in the same conditions as in Comparative Example 1 again after the reaction was conducted continuously in the conditions of Example 1, 2, 3 and the introduction of $CO_2$ was halted. The result of the reaction is summarized in Table 1.

Comparative Example 3

The oxidation reaction of methacrolein was conducted in the same conditions as in Comparative Example 2 except that the temperature of the heat materials was increased to 300° C. The result of the reaction is summarized in Table 1.

Example 4

The reaction to prepare methacrylic acid by oxidation of methacrolein was conducted by the same way as in Comparative Example 3 except that the content of nitrogen is reduced to 5 mol % and 5 mol % of $CO_2$ was introduced in the composition of the inlet gas which was fed into the reactor. The result of the reaction is shown in Table 1.

TABLE 1

|  | Temperature of Heat Medium (° C.) | Concentration of Co-, (mol%) | Conversion Rate of Methacrolein | Selectivity for Methacrylic Acid (%) |
|---|---|---|---|---|
| Comparative Example 1 | 290 | 0 | 72.4 | 79.1 |
| Example 1 | 290 | 5 | 72.0 | 82.7 |
| Example 2 | 290 | 9 | 70.2 | 83.7 |
| Example 3 | 290 | 5 | 69.2 | 86.4 |
| Comparative Example 2 | 290 | 0 | 75.2 | 80.6 |
| Comparative Example 3 | 300 | 0 | 79.5 | 79.4 |
| Example 4 | 300 | 5 | 73.9 | 83.8 |

As described in the above paragraphs, the preparation method of the present invention has an effect of producing methacrylic acid with high selectivity.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method for producing methacrylic acid by gas phase oxidation of methacrolein, comprising:
   injecting a feed gas comprising methacrolein, oxygen and $CO_2$ in the presence of a catalyst of a general formula of $P_a Mo_{11} V_b X_c Y_d O_e$, wherein X is one or more elements selected from the group of alkaline metal and Tl element, and wherein Y is one or more elements selected from the group consisting of Cu, Pb, Sb, Cr and Ce, and wherein a is 0.8–1.6; b is 0.6–2; c is 0.8–2.2; d is 0.1–0.8; and e is a necessary value of valency in line with the general formula; and
   wherein $CO_2$ comprises about 4 to about 20 mol % of the feed gas.

2. The method of claim 1, further comprising carrying out the oxidation reaction at a reaction temperature of about 260–330° C.

3. The method of claim 1, wherein $CO_2$ comprises about 5 to about 15 mol % of the feed gas.

4. The method of claim 1, further comprising carrying out the oxidation reaction at a space velocity of about 700–2000 $hr^{-1}$.

5. The method of claim 1, further comprising carrying out the oxidation reaction with a methacrolein concentration of about 2–5 mol %.

6. The method of claim 1, further comprising carrying out the oxidation reaction with a reaction pressure of about 0.5–5 kg in terms of absolute pressure.

7. The method of claim 1, further comprising carrying out the oxidation reaction with a molar ratio of about 2.0–3.5 between oxygen and methacrolein.

* * * * *